(12) United States Patent
Moriya

(10) Patent No.: US 8,194,958 B2
(45) Date of Patent: Jun. 5, 2012

(54) IMAGE DISPLAY DEVICE

(75) Inventor: Yoshiyuki Moriya, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 738 days.

(21) Appl. No.: 12/306,527

(22) PCT Filed: May 1, 2007

(86) PCT No.: PCT/JP2007/059305
§ 371 (c)(1),
(2), (4) Date: Dec. 24, 2008

(87) PCT Pub. No.: WO2008/001546
PCT Pub. Date: Jan. 3, 2008

(65) Prior Publication Data
US 2009/0310843 A1    Dec. 17, 2009

(30) Foreign Application Priority Data
Jun. 26, 2006 (JP) .................................. 2006-175302

(51) Int. Cl.
*G06K 9/00* (2006.01)
(52) U.S. Cl. ........ 382/130; 382/128; 382/129; 382/131; 382/132; 382/173; 382/219; 382/220; 382/282
(58) Field of Classification Search .......... 382/128–132, 382/922, 173, 282, 219, 220; 715/530, 513, 715/86, 780, 507, 506, 505; 378/4–27
See application file for complete search history.

(56) References Cited

U.S. PATENT DOCUMENTS

| 6,058,322 A * | 5/2000 | Nishikawa et al. ........... 600/408 |
| 6,088,473 A * | 7/2000 | Xu et al. ....................... 382/132 |
| 7,406,187 B2 * | 7/2008 | Sato et al. ..................... 382/128 |
| 7,620,229 B2 * | 11/2009 | Oosawa ........................ 382/130 |
| 2003/0095697 A1 * | 5/2003 | Wood et al. ................... 382/131 |
| 2004/0081342 A1 * | 4/2004 | Sato .............................. 382/128 |
| 2004/0184647 A1 * | 9/2004 | Reeves et al. ................. 382/131 |

FOREIGN PATENT DOCUMENTS

| JP | 6-175245 A | 6/1994 |
| JP | 8-76741 A | 3/1996 |
| JP | 8-294485 A | 11/1996 |
| JP | 2001-137230 A | 5/2001 |
| JP | 2001-299733 A | 10/2001 |
| JP | 2003-99021 A | 4/2003 |
| JP | 2003-310586 A | 11/2003 |
| JP | 2004-09617 A | 3/2004 |
| JP | 2004-096417 A | 3/2004 |

OTHER PUBLICATIONS

Chapter I International Preliminary Report on Patentability and Written Opinion, mailed Feb. 12, 2009, issued in corresponding International Application No. PCT/JP2007/059305, 6 pages.

\* cited by examiner

*Primary Examiner* — Georgia Y Epps
*Assistant Examiner* — Sultan Chowdhury
(74) *Attorney, Agent, or Firm* — Sughrue Mion, PLLC

(57) ABSTRACT

An image display device that includes: a region-of-interest setting section that sets regions-of-interest respectively for multiple medical images representing a photographed subject; a difference image creating section that creates a difference image representing a difference between images of the regions-of-interest set by the region-of-interest setting section; and an image displaying section that displays the difference image as well as the images arranged side by side.

7 Claims, 12 Drawing Sheets

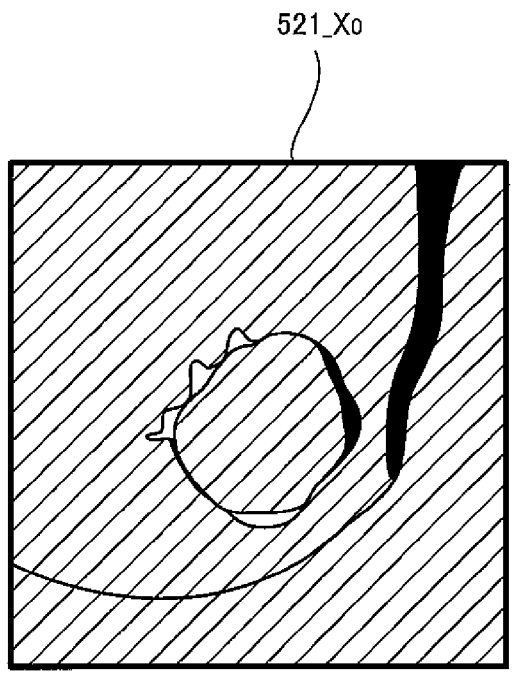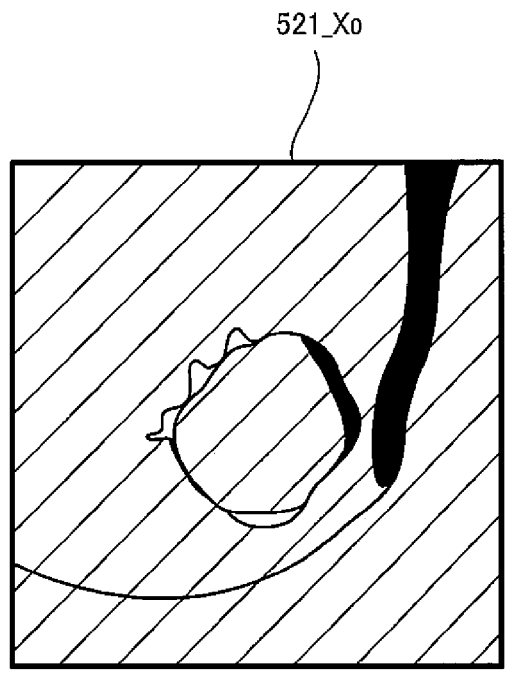
FIG. 10A
521_X0
FIG. 10B
521_X0

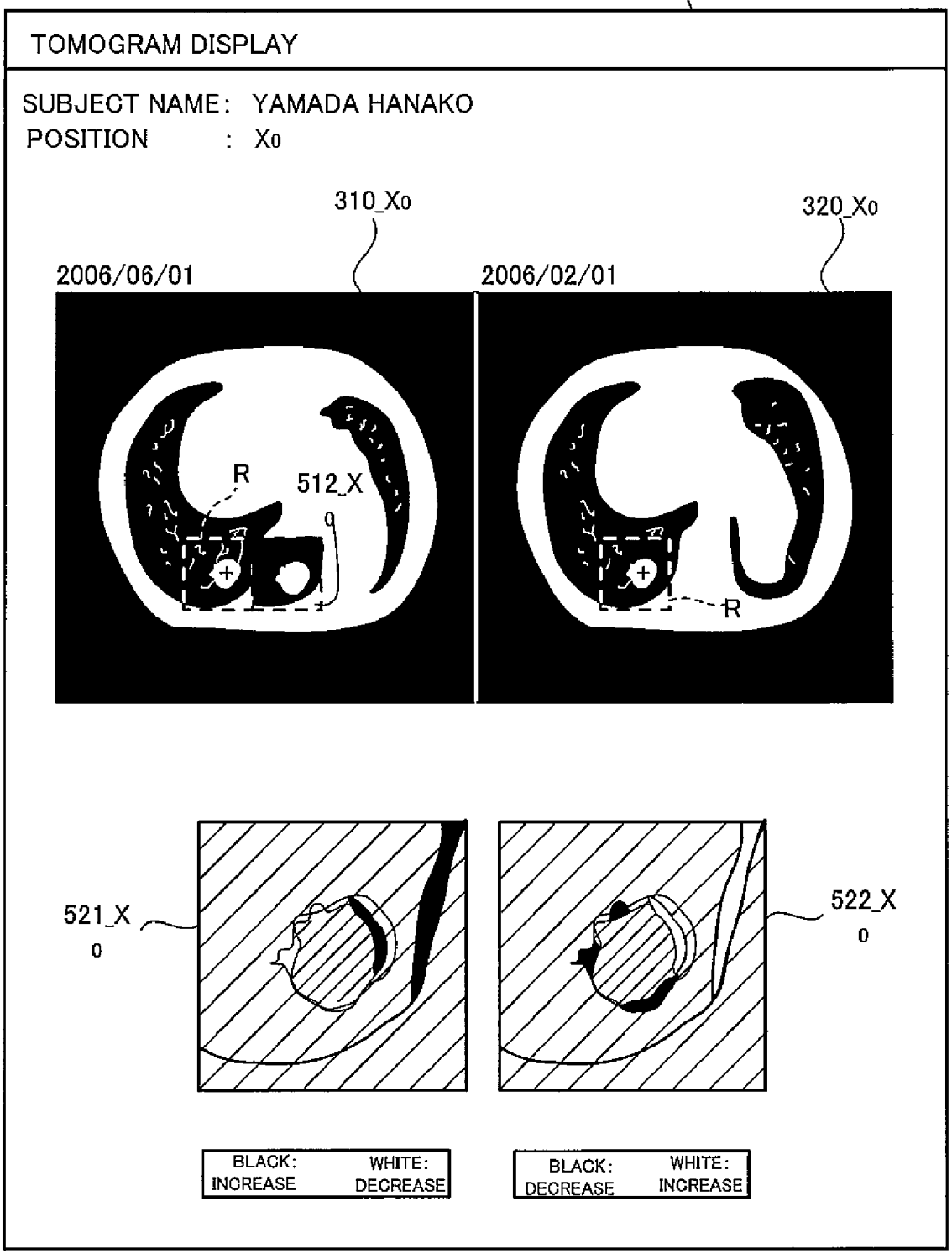

IMAGE DISPLAY DEVICE

BACKGROUND OF THE INVENTION

1. Field of the Invention

The present invention relates to an image display device that displays medical images representing a photographed subject.

2. Description of the Related Art

In the medical field, it is widely practiced to utilize medical images representing a photographed internal body of a subject by using radiation or the like for the diagnosis of symptoms of the subject. Utilizing the medical images for the diagnosis enables a person in the medical field to grasp the stages of symptoms of the subject or the like without causing external damage to the subject and obtain necessary information to determine treatment plans or the like.

Further, in recent years, such devices as CR (Computed Radiography) for obtaining digitalized medical images by using radiation, CT (Computerized Tomography) for obtaining tomograms of the subject by using radiography, and MRI (Magnetic Resonance Imaging) for obtaining tomograms of the subject by using strong magnetic fields are becoming widely used, and digitalized medical images are becoming commonly used instead of medical images using conventional X-ray films or the like. With the digitalization of medical images, it is possible to collectively manage the medical images together with digitalized medical records of the subject, and to share the medical images and the records among hospitals or the like via network. Thus, even though a clinic or a hospital where the subject receives treatment is changed, the medical images and the medical records showing the past history of disease of the subject can be utilized.

Also, with the digitalization of medical images, applying image processing on the medical images becomes easy, thereby multiple medical images of an identical subject photographed at different times are displayed arranged side-by-side on a monitor, and an image of a region-of-interest suspected as a lesion on the medical images is cut out to be enlarged on the monitor. However, even if the medical images are displayed arranged side-by-side or the image of the region-of-interest is enlarged, there is a problem that it is hard to recognize variations when increase and decrease of the lesion is little.

In this regard, Japanese Patent Application Publication (JP-AP) No. 2004-96417 describes a technique of displaying a difference image representing a difference between medical images on a monitor. By checking the difference image displayed on the monitor, a doctor and a subject can easily confirm the degree of increase and decrease of a lesion.

However, it is very difficult to photograph a subject in the exact same position at each different time. Thus, in the technique described in JP-AP No. 2004-96417, there is a problem that a slight displacement in the positions of the subject between the medical images appears on the difference image, thereby a difference caused by variations of the lesion and a difference caused by the position-displacement are mixed on the difference image.

Also, Japanese Patent Application Publication (JP-AP) No. 6-175245 discloses a method of matching positions between multiple images. Creating a difference image after matching positions between the multiple images with the use of the technique described in JP-AP No. 6-175245, the inconvenience of position-displacement appearance on the difference image can be reduced.

However, even with application of the techniques described in JP-AP No. 2004-96417 and JP-AP No. 6-175245, a slight displacement in postures of a subject and variations in the body size of the subject, which are hard to be corrected only through position-displacement correction processing, appear on a difference image. As a result, on the difference image, not only variations of the lesion, but also differences due to various kinds of causes are mixed. Therefore, it is hard to recognize variations of the lesion by checking the difference image or comparing the medical images.

SUMMARY OF THE INVENTION

The present invention has been made in view of the above circumstances and provides an image display device that enables a user to reliably recognize variations of a lesion or the like shown in respective multiple medical images.

An image display device of the present invention includes:

a region-of-interest setting section that sets regions-of-interest respectively for multiple medical images representing a photographed subject;

a difference image creating section that creates a difference image representing a difference between images of the regions-of-interest set by the region-of-interest setting section; and an image displaying section that displays the difference image as well as the images arranged side by side.

According to the image display device of the present invention, when regions-of-interest are respectively set for multiple medical images, images of these regions-of-interest are displayed arranged side-by-side and a difference image representing a difference between these images is also displayed. The user can roughly recognize variations in them by comparing the images. And by checking the difference image, the user can reliably recognize an in-depth different point that is hard to be noticed only by comparing the images.

In the image display device of the present invention, it is preferable that the region-of-interest setting section sets a region in response to an operation as the region-of-interest for a part of the multiple medical images, and for the rest of medical images except the part of the medical images, detects a region corresponding to the region in response to the operation to set as the region-of-interest.

According to this favorable image display device of the present invention, it is possible to save labor of setting regions-of-interest each by each for the multiple medical images.

Here, "a region corresponding to the region in response to the operation" may be merely a region having a same coordinate as the region in response to the operation, or a region of which position is matched by image-matching processing or the like.

It is preferable that the image display device of the present invention further comprises a position-displacement correcting section that corrects position-displacement of an image between the regions set by the region-of-interest setting section, and the difference image creating section creates the difference image with the use of the image of which position-displacement has been corrected by the position-displacement correcting section.

Traditionally, image-matching processing for correcting position-displacement between images has been known widely. By creating a difference image with the use of an image of which position-displacement has been corrected by using this image-matching processing or the like, the user can accurately recognize a different point between the images.

In the image display device of the present invention, it is preferable that the difference image creating section creates the difference image and an inverse image of which concentration is inverted from the difference image, and the image displaying section displays the difference image and the inverse image arranged side by side.

By displaying the difference image and the inverse image arranged side by side, the user can surely recognize both increased and decreased areas between the images.

In the image display device of the present invention, it is preferable that the image displaying section displays the medical images and an image of the region-of-interest set in another medical image side-by-side with the region-of-interest in the medical image.

By displaying the image of the region-of-interest that has been set in another medical image side-by-side with the region-of-interest in the medical image, the user can recognize positions of these regions-of-interest in the medical image.

In the image display device of the present invention, it is preferable that the multiple medical images are photographed at different times for an identical subject.

According to the favorable image display device of the present invention, it is possible to easily recognize variations or the like in the size of a lesion of the subject.

In the image display device of the present invention, it is preferable that the respective medical images correspond to a tomogram constituting a tomogram group when the subject is sliced at a plurality of slicing positions along a predetermined direction;

the multiple medical images correspond to a set of tomograms having a common slicing position, which forms a different tomogram group;

the region-of-interest setting section sets the region-of-interest for a tomogram in a set of the sets obtained at the multiple slicing positions, and sets as the region-of-interest, for tomograms in another sets, a region corresponding to the region that has been set; and the image displaying section temporarily displays for a set, images of the regions-of-interest in tomograms of the set and a difference image between the images arranged side by side, and further, in response to a change operation, displays images of the regions-of-interest in tomograms of another sets as well as a difference image between the images arranged side-by-side.

By changing a set to display in response to an operation, the user can easily recognize images and difference images at various slicing positions and grasp the shape and the size of a lesion three-dimensionally.

It is preferable that the image display device of the present invention further includes a gradation adjusting section that adjusts in response to an operation, gradation of a difference image displayed on the image displaying section.

By adjusting gradation of the difference image, it is possible to find a different point in the image without fail.

The present invention enables the user to reliably recognize variations of a lesion or the like shown in multiple medical images.

BRIEF DESCRIPTION OF THE DRAWINGS

FIG. 10 illustrates how gradation is adjusted in a difference image.

FIG. 12 illustrates an example of a tomogram display screen on which clipped images, a difference image, and an inverse image are displayed.

DETAILED DESCRIPTION OF THE INVENTION

Embodiments of the present invention will be described below with reference to the accompanying drawings.

Figure 1:
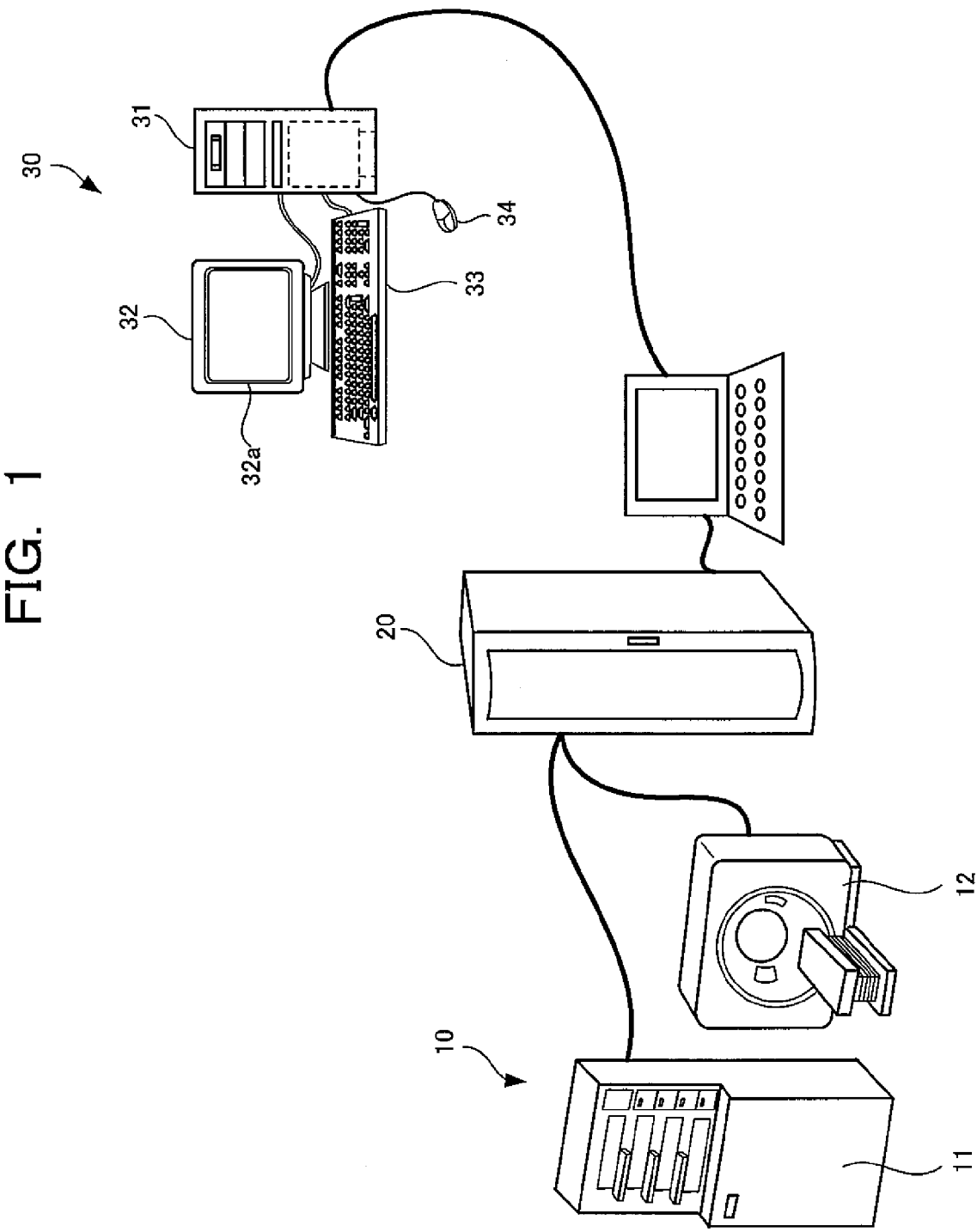
FIG. 1 schematically illustrates the structure of a medical diagnosis system in which one embodiment of the present invention is implemented.

FIG. 1 schematically illustrates the structure of a medical diagnosis system in which one embodiment of the present invention is implemented.

The medical diagnosis system depicted in FIG. 1 includes an image generation unit 10 that creates medical images by photographing internal body of a subject, a management server 20 that stores medical images and medical records, and a diagnosis unit 30 that displays medical images. The image generation unit 10 and the management server 20 as well as the management server 20 and the diagnosis unit 30 are connected to each other via a network.

At this medical diagnosis system, an ID number for identifying the subject is assigned to each subject at the initial visit, and the ID number and its corresponding medical record showing the name, age, history of disease or the like are registered with the management server 20.

The image generation unit 10 includes a CR unit 11 for applying radiation to a subject and creating a digital medical image by reading the radiation passing through the subject, a MRI unit 12 for creating a tomogram of the subject by using a strong magnetic field and radio waves, a CT unit (not shown) for creating a tomogram of the subject by using radiation, and an ultrasonic unit (not shown) for creating a medical image by reading an ultrasonic echo. The medical images created at the image generation unit 10 are transmitted to the management server 20 along with an ID number for identifying the subject of the medical images.

When the medical images and the ID number are transmitted from the image generation unit 10, the management server 20 stores the medical images by matching them with the ID number. That is, in the management server 20, the ID number, the medical record of the subject with the assigned ID number, and the matched medical images of the subject are registered.

In appearance, the diagnosis unit 30 includes a main unit 31, an image display unit 32 for displaying an image on a display screen 32a in response to an instruction from the main unit 31, a keyboard 33 for inputting various kinds of information to the main unit 31 in response to key operations, and a mouse 34 for specifying a position on the display screen 32a and inputting an instruction in accordance with, for example, an icon displayed in the position.

When a user inputs a name and an ID number of the subject with the use of the mouse 34 or the like of the diagnosis unit 30, the inputted contents is transmitted to the management server 20. The management server 20 then transmits a medical image and a medical record associated with the name and the ID number of the subject transmitted from the diagnosis unit 30 to the diagnosis unit 30. In the diagnosis unit 30, the medical image sent from the management server 20 is displayed on the display screen 32*a*. By checking the medical image displayed on the display screen 32*a* of the diagnosis unit 30, the user can diagnose the condition of the subject, without causing external damage to the subject.

The user diagnoses the condition of the subject by watching the medical image displayed on the display screen 32*a* of the diagnosis unit 30, and edits the medical record with the use of the mouse 34 and the keyboard 33. The edited medical record is transmitted to the management server 20 and the medical record having been stored in the management server 20 is updated to the new medical record sent from the diagnosis unit 30.

The medical diagnosis system depicted in FIG. 1 is basically configured as described above.

The medical diagnosis system as one embodiment of the present invention is characterized by operation procedures to be carried out by the diagnosis unit 30. In the following, the diagnosis unit 30 will be described in detail.

Figure 2:
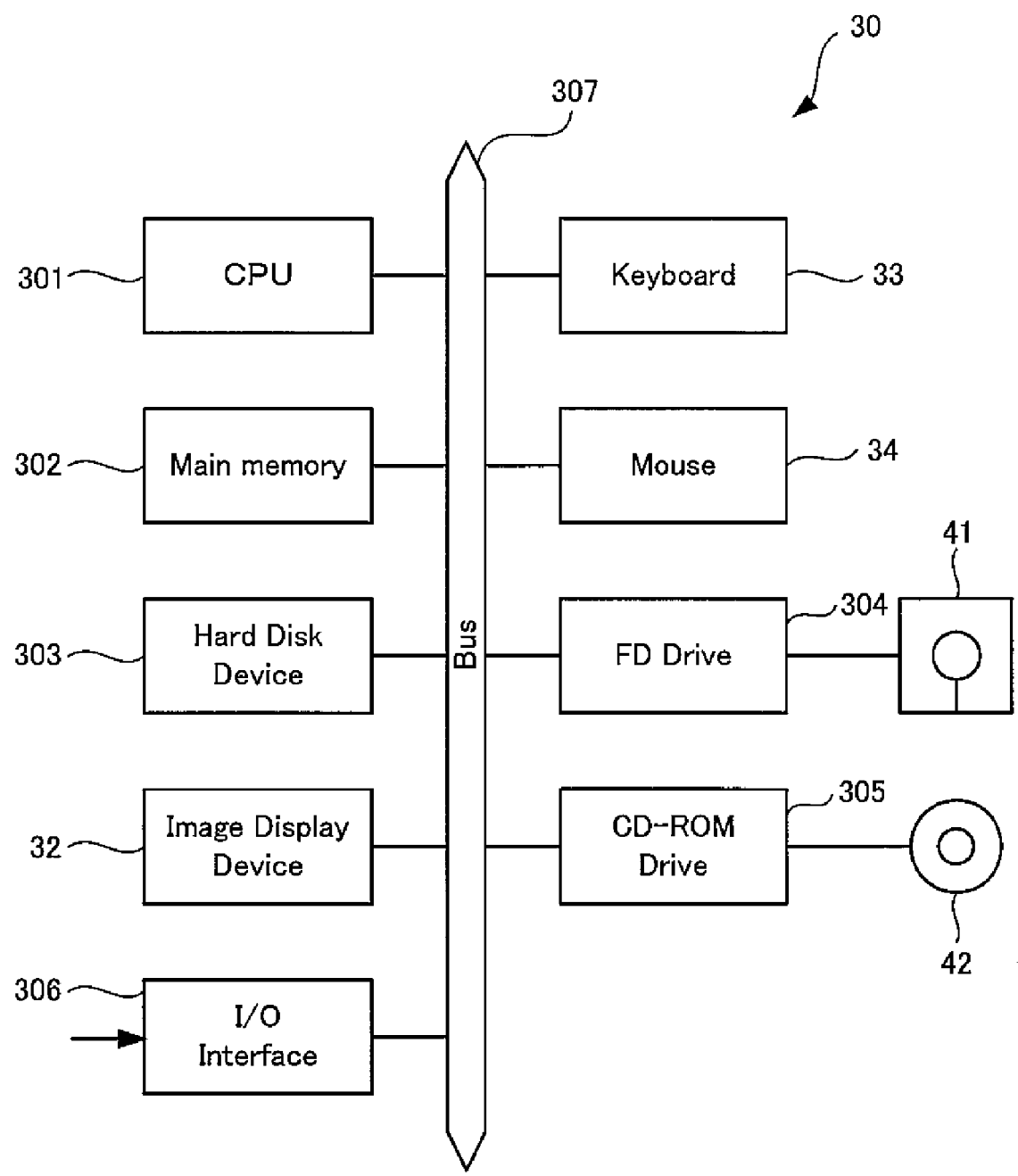
FIG. 2 illustrates the hardware structure of the medical diagnosis unit.

FIG. 2 illustrates the hardware structure of the medical diagnosis unit 30.

As depicted in FIG. 2, the main unit 31 of the diagnosis unit 30 is internally equipped with a CPU 301 for executing various kinds of programs, a main memory 302 for reading and expanding a program stored in a hard disk unit 303 and a FD 41 to be executed by the CPU 301, the hard disk unit 303 for storing various kinds of programs and data or the like, a FD drive 304 for accessing the FD 41, a CD-ROM drive 305 for accessing a CD-ROM 42, and an I/O interface 306 for receiving image date and so on from the management server 20 and transmitting various kinds of instructions to the management server 20. These various kinds of elements and furthermore, the image display unit 32, the keyboard 33, the mouse 34, which are also illustrated in FIG. 1, are connected to one another via a bus 307.

Here, the CD-ROM 42 stores a medical image display program 100 (See FIG. 3) for building in the diagnosis unit 30 one embodiment of the image display unit of the present invention.

Figure 3:
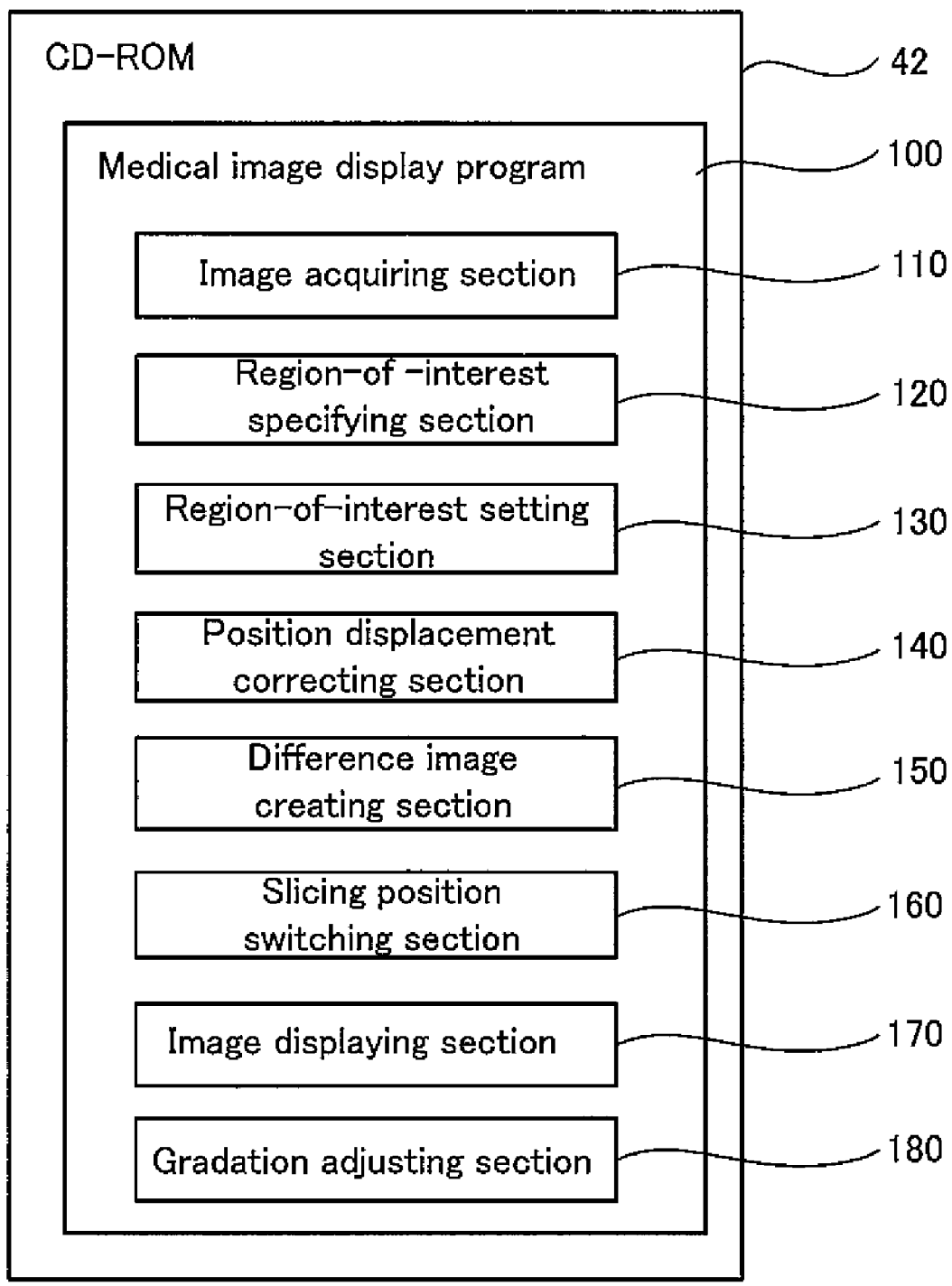
FIG. 3 is a conceptual diagram of a CD-ROM.

FIG. 3 is a conceptual diagram of a CD-ROM 42.

As illustrated in FIG. 3, the medical image display program 100 stored in the CD-ROM 42 is constituted of an image acquiring section 110, a region-of-interest specifying section 120, a region-of-interest setting section 130, a position-displacement correcting section 140, a difference image creating section 150, a slicing position switching section 160, an image displaying section 170, and a gradation adjusting section 180.

The CD-ROM 42 is inserted into the CD-ROM drive 305 of the diagnosis unit 30, and the medical image display program 100 stored in the CD-ROM 42 is uploaded to the diagnosis unit 30 and stored in the hard disk unit 303. Launching and executing this medical image display program 100 constructs in the diagnosis unit 30 a medical image display unit 200 (See FIG. 4) as one embodiment of the medical image display device of the present invention.

Additionally, although in the above-description, the CD-ROM 42 is exemplified as a storage medium for storing the medical image display program 100, the storage medium for storing the medical image display program 100 is not limited to a CD-ROM, but also it may be any other storage media such as an optical disk, an MO, an FD, and a magnetic tape. Furthermore, the medical image display program 100 may be directly supplied to the diagnosis unit 30 via the I/O interface 306 without using any storage media.

Details of each section of the medical image display program 100 will be explained along with the action of each section of the medical image display unit 200.

Figure 4:
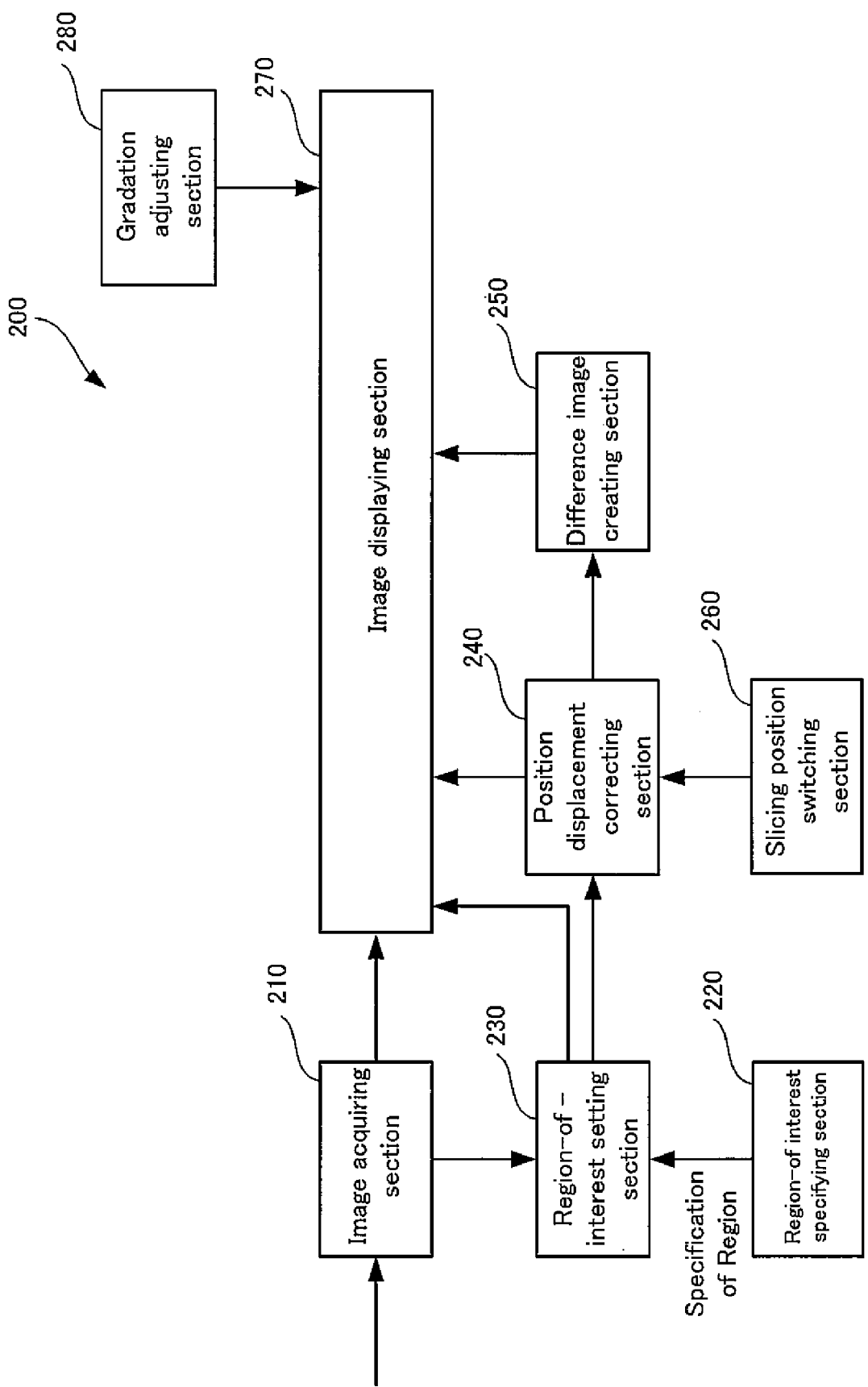
FIG. 4 is a functional block diagram of a medical image display unit.

FIG. 4 is a functional block diagram of the medical image display unit 200.

The medical image display unit 200 includes an image acquiring section 210, a region-of-interest specifying section 220, a region-of-interest setting section 230, a position-displacement correcting section 240, a difference image creating section 250, a slicing position switching section 260, an image displaying section 270, and a gradation adjusting section 280.

The image acquiring section 210, the region-of-interest specifying section 220, the region-of-interest setting section 230, the position-displacement correcting section 240, the difference image creating section 250, the slicing position switching section 260, the image displaying section 270, and the gradation adjusting section 280 of the medical image display unit 200 have one-to-one correspondence with the image acquiring section 110, the region-of-interest specifying section 120, the region-of-interest setting section 130, the position-displacement correcting section 140, the difference image creating section 150, the slicing position switching section 160, the image displaying section 170, and the gradation adjusting section 180 of the medical image display program 100 depicted in FIG. 3.

The respective sections depicted in FIG. 4 are formed by a combination of computer hardware and an OS or an application program to be executed by the computer, while the respective sections of the medical image display program 100 depicted in FIG. 3 are formed only by an application program.

Figure 5:
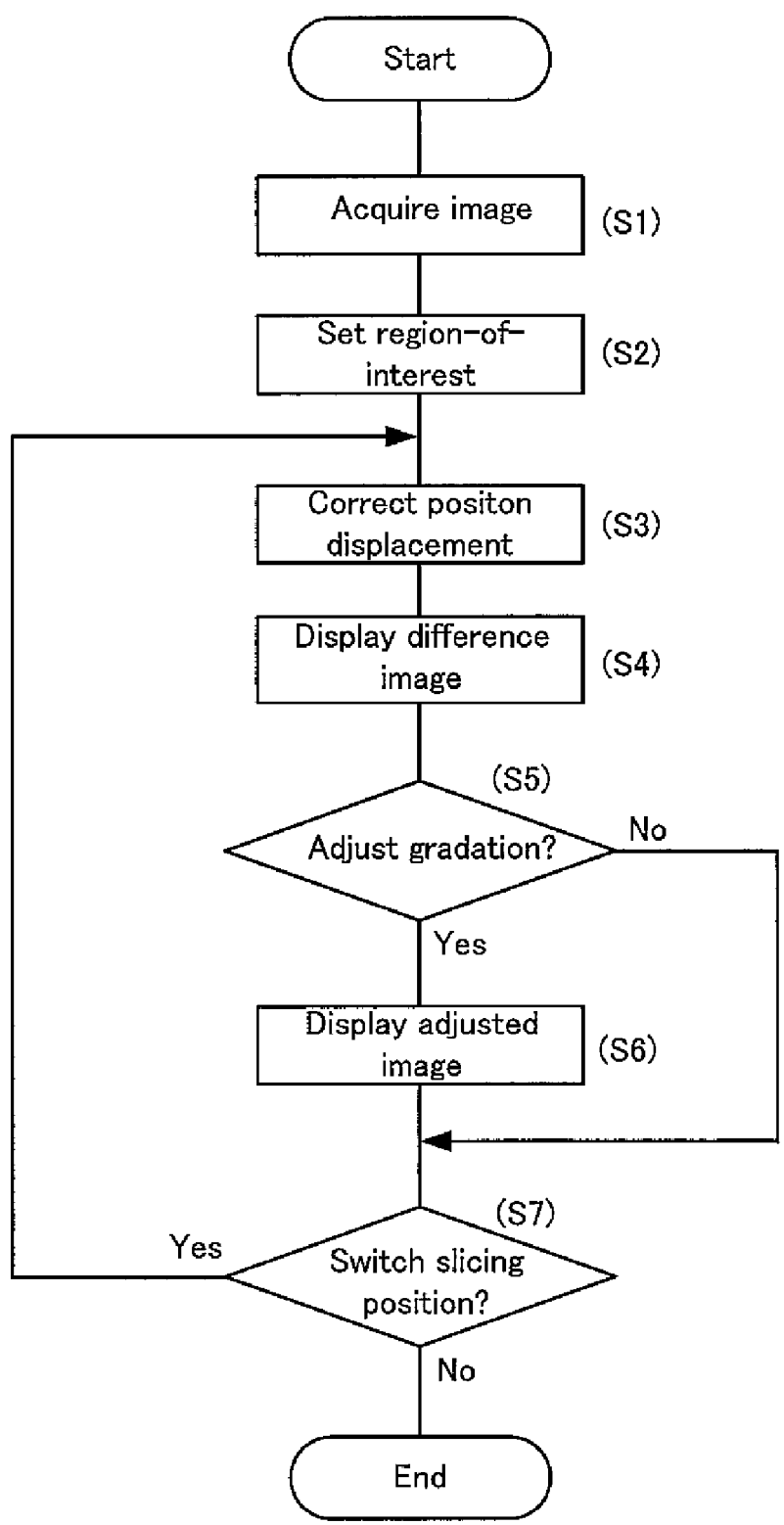
FIG. 5 is a flowchart illustrating a series of processing carried out in the medical image display unit depicted in FIG. 4, starting from acquisition of medical images from the management server, and ends with displaying the acquired medical images.

FIG. 5 is a flowchart illustrating a series of processing to be carried out in the medical image display unit 200 depicted in FIG. 4, starting from acquisition of medical images from the management server 20, and ends with displaying the acquired medical images.

Hereinafter, following the flowchart in FIG. 5, an explanation will be given about the action of each section of the medical image display unit 200 illustrated in FIG. 4, which also explains each section of the medical image display program 100 illustrated in FIG. 3.

When the user inputs a name and an ID number of the subject for diagnosis by using the mouse 34 and the keyboard 33 shown in FIG. 1, the inputted contents is transmitted to the management server 20 via the I/O interface 306 in FIG. 2. From the management server 20, a medical image and a medical record matched with the name and ID number transmitted from the diagnosis unit 30 are transmitted toward the diagnosis unit 30.

The medical image transmitted from the management server 20 is acquired at the image acquiring section 210 shown in FIG. 4 (step S1 in FIG. 5).

Figure 6:
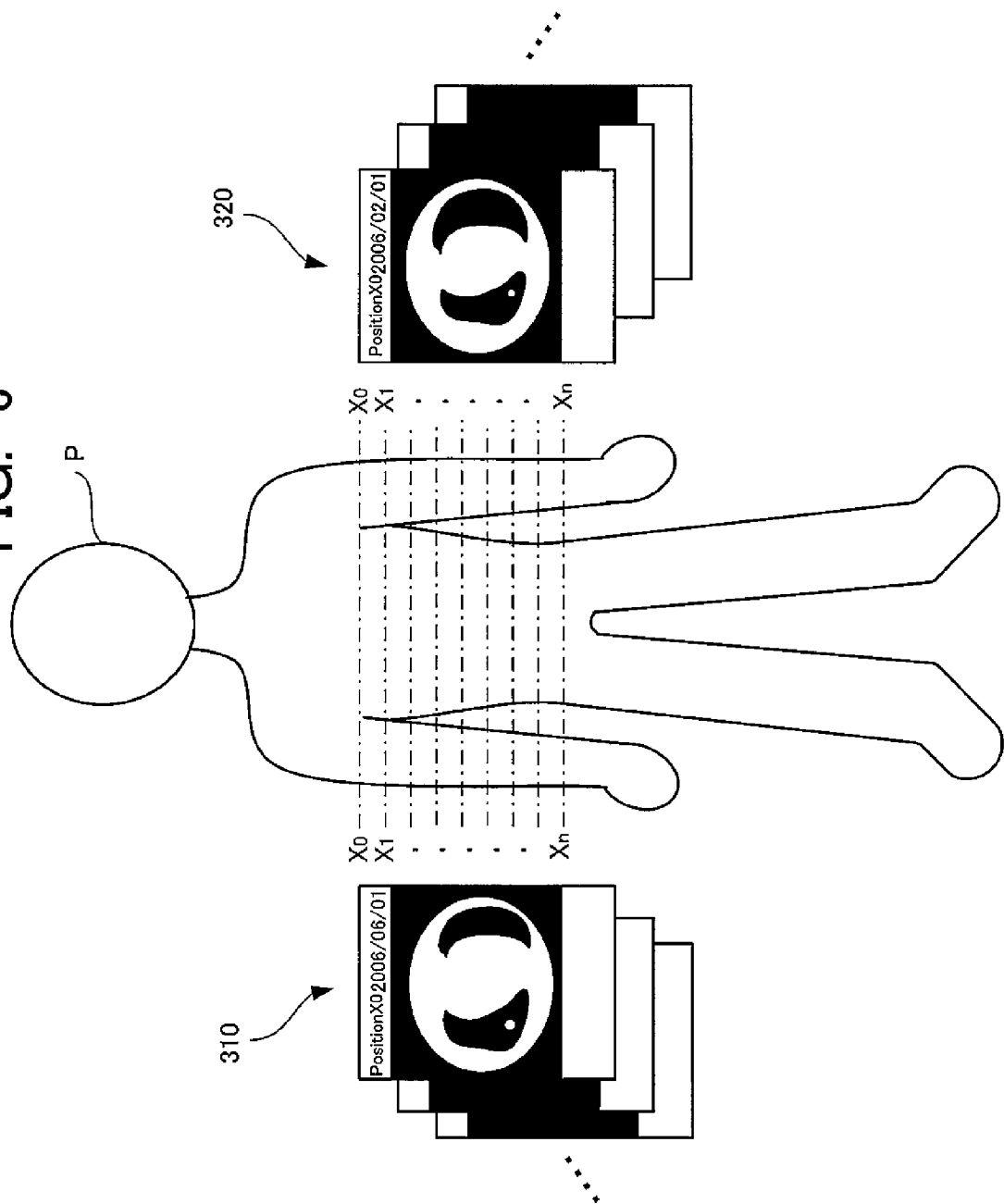
FIG. 6 illustrates medical images transmitted from the management server.

FIG. 6 illustrates medical images transmitted from the management server 20.

At the MRI unit 12 depicted in FIG. 1, each cross-section of a subject P is photographed when the subject P is sliced at multiple slicing positions of X0 to Xn that includes from the chest to the base of the ankle. In the present embodiment, the identical subject P is photographed twice by using the MRI unit 12 at different times, and in each photographing, tomogram groups 310, 320 composed of multiple tomograms are created and stored in the management server 20. The image acquiring section 210 acquires the tomogram groups 310, 320 of the two different times, and the acquired tomogram groups 310, 320 are transmitted to the image displaying section 270 and the region-of-interest setting section 230.

The image displaying section 270 displays a tomogram display screen 410 (See FIG. 7) including the tomogram groups 310, 320 transmitted from the image acquiring section 210 on the display screen 32a depicted in FIG. 1. The image displaying section 270 corresponds to one example of the image displaying section according to the present invention.

Figure 7:
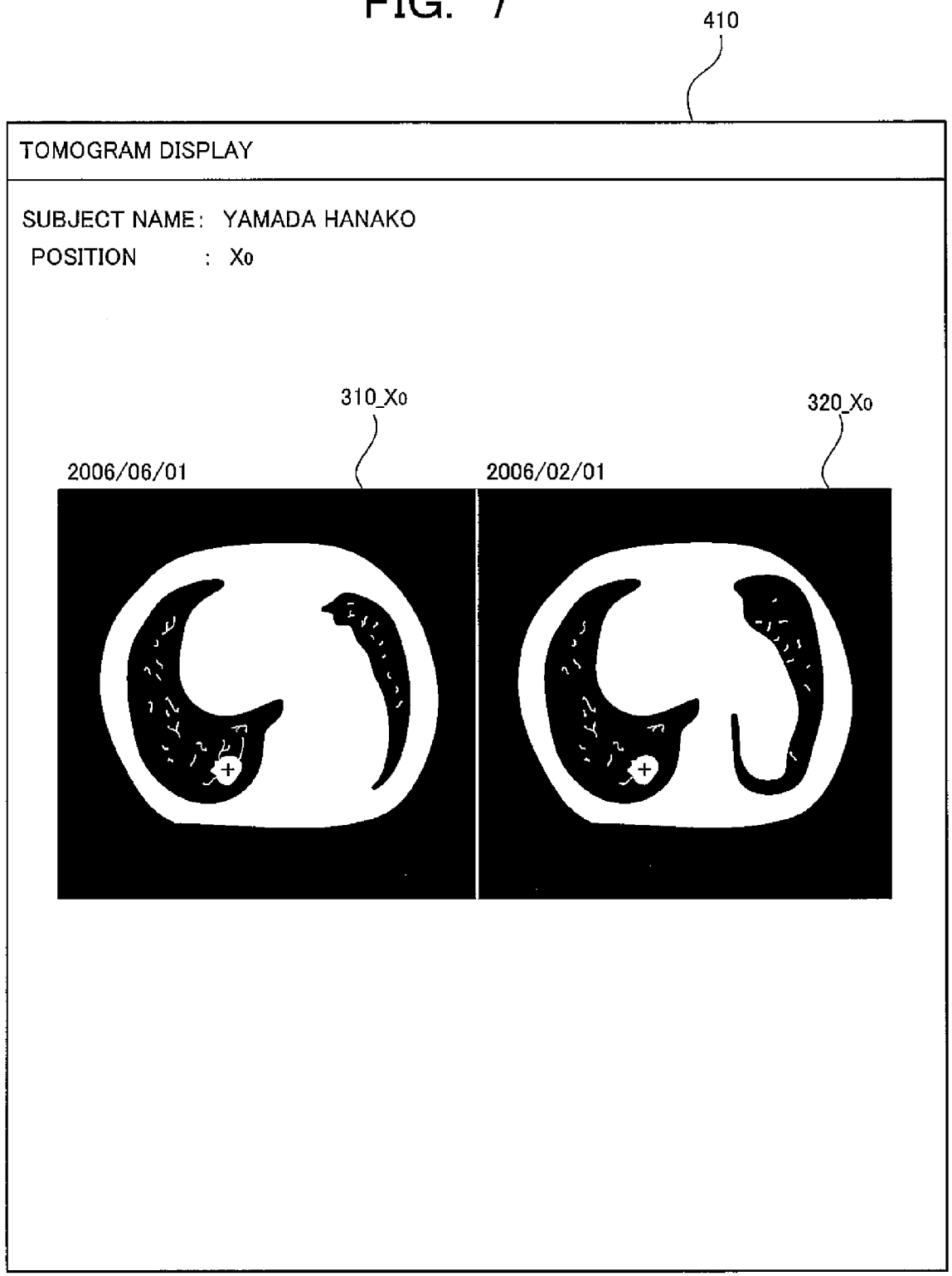
FIG. 7 illustrates an example of a tomogram display screen.

FIG. 7 illustrates an example of the tomogram display screen.

On the tomogram display screen 410 illustrated in FIG. 7, the tomograms 310_X0, 320_X0 at a slicing position X0 are displayed out of the tomograms constituting the tomogram groups 310, 320. Also the slicing position of these tomograms 310_X0, 320_X0, the date of photographing, and the name of a subject or the like are displayed.

These two tomograms 310_X0, 320_X0 are images representing cross-sections of the identical subject photographed at the same slicing position at different times, so that by comparing these, variations of a lesion or the like can be confirmed. However, if the variations of the lesion are little, there is a problem that the variations are hard to be recognized only through the comparison of these images.

At the medical image display unit 200 in the present embodiment, firstly, a region-of-interest suspected as a lesion on the tomograms 310_X0, 320_X0 is set as follows (step S2 in FIG. 5). When the user checks the tomograms 310_X0, 320_X0 on the tomogram display screen 410 and clicks a region-of-interest suspected as a lesion in one of the tomograms 310_X0 and 320_X0 with the use of the mouse 34 illustrated in FIG. 1, information of clicked position is transmitted from the region-of-interest specifying section 220 to the region-of-interest setting section 230 illustrated in FIG. 4.

The region-of-interest setting section 230 temporarily determines between the tomograms 310_X0 and 320_X0, for one image on which the interest area has been specified, a region within a predetermined range having the specified interest area as the center, as a region-of-interest; whereas for the other image on which an interest area has not been specified, determines a region having the same position as the temporarily determined region-of-interest for the one image, as a region-of-interest. The region-of-interest setting section 230 corresponds to an example of the region-of-interest setting section of the present invention. The position of the temporarily determined region-of-interest is transmitted to the image displaying section 270.

In step S2 in FIG. 5, when the user specifies respective interest areas on both tomograms 310_X0 and 320_X0 on the tomogram display screen 410, regions-of-interest are temporarily determined based on the respective specified interest areas.

The image displaying section 270 encloses the region-of-interest temporarily determined by the region-of-interest setting section 230 by frame, on the tomogram displaying section 410 depicted in FIG. 7.

Figure 8:
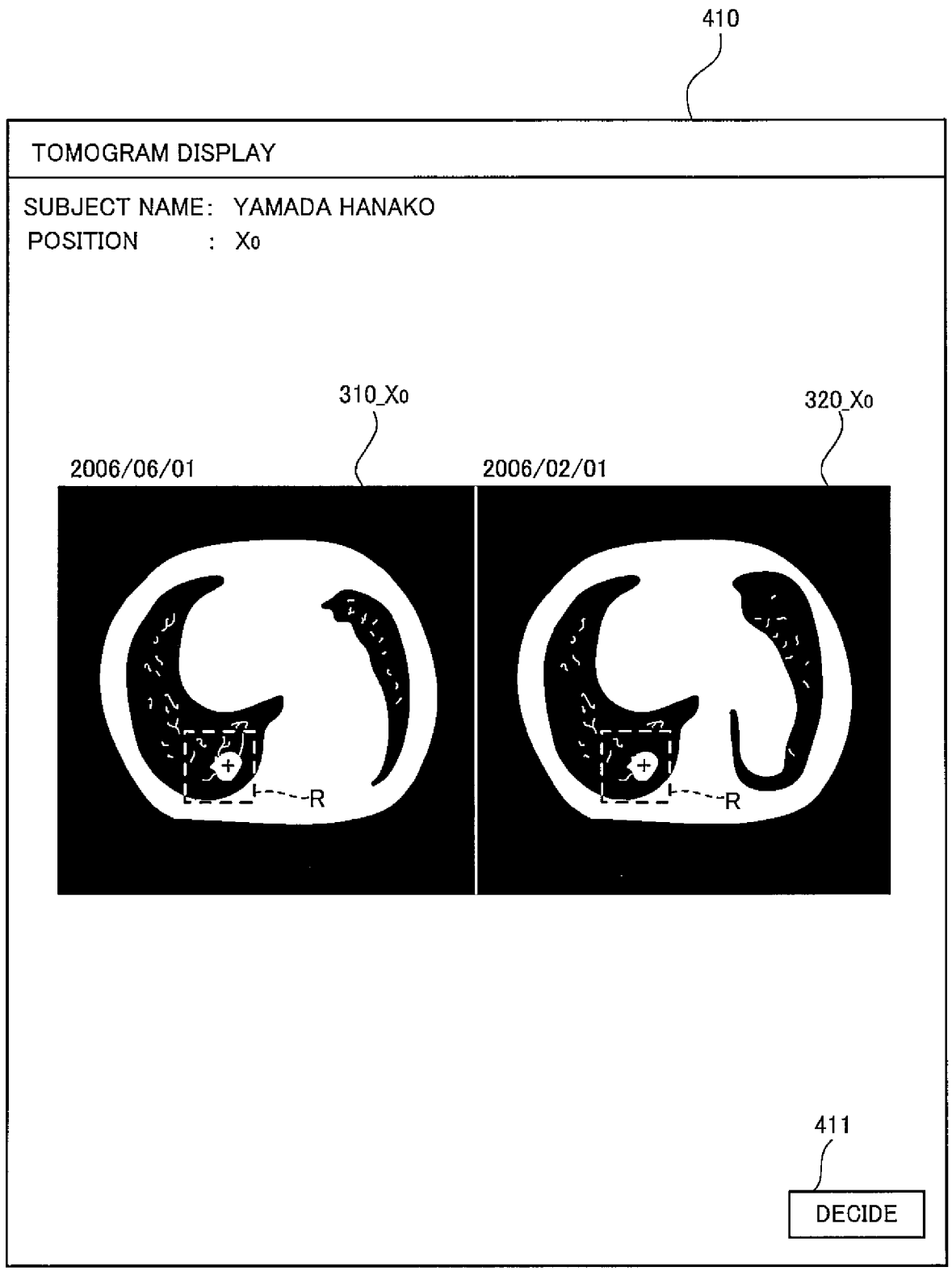
FIG. 8 illustrates an example of a tomogram display screen on which a region-of-interest is enclosed by frame.

FIG. 8 illustrates an example of a tomogram display screen on which a region-of-interest is enclosed by frame.

As depicted in FIG. 8, in the tomograms 310_X0, 320_X0 on the tomogram display screen 410, the regions temporarily determined as the regions-of-interest are enclosed by frame R. If a lesion is not included in the regions enclosed by the frame R, the user adjusts the position of the frame R with the use of the mouse 34 or the like depicted in FIG. 1. When the user presses down a decide button 411, the position of the regions enclosed by the frame R at that time are transmitted from the region-of-interest specifying section 220 to the region-of-interest setting section 230.

The region-of-interest setting section 230 determines the position transmitted from the region-of-interest specifying section 220 as a region-of-interest for the tomograms 310_X0, 320_X0, and for all tomograms in the tomogram groups 310 and 320 that include the tomograms 310_X0, 320_X0, a region having the same position as the determined region-of-interest, as the region-of-interest as well. The position of the determined region-of-interest and the tomogram groups 310, 320 are transmitted to the position-displacement correcting section 240.

The position-displacement correcting section 240 cuts out an image (hereinafter, referred as a clipped image) of the region-of-interest set for the respective tomograms 310_X0, 320_X0 at the slicing position X0, which are currently displayed, and corrects position-displacement of these clipped images (step S3 in FIG. 5). The position-displacement correcting section 240 corresponds to one example of the position-displacement correcting section of the present invention. Regarding a technique for correcting position-displacement between images, techniques such as image matching processing has been widely known so that detailed explanation is omitted. The clipped images of which position-displacement has been corrected are transmitted to the image displaying section 270 and the difference image creating section 250.

At the difference image creating section 250, of the two clipped images transmitted from the position-displacement correcting section 240, a difference image is created by subtracting the clipped image of the tomogram 320_X0 having the previous photographing date from the clipped image of the tomogram 310_X0 having the recent photographing date; whereas an inverse image is created by subtracting the clipped image of the tomogram 310_X0 having the recent photographing date from the clipped image of the tomogram 320_X0 having the previous photographing date. These created difference image and inverse image are transmitted to the image displaying section 270. The difference image creating section 250 corresponds to one example of the difference image creating section of the present invention.

The image displaying section 270 displays these two clipped images transmitted from the position-displacement correcting section 240, arranged side-by-side on the tomogram display screen 410 depicted in FIG. 8, together with the difference image and the inverse image transmitted from the difference image creating section 250 (step S4 in FIG. 5).

Figure 9:
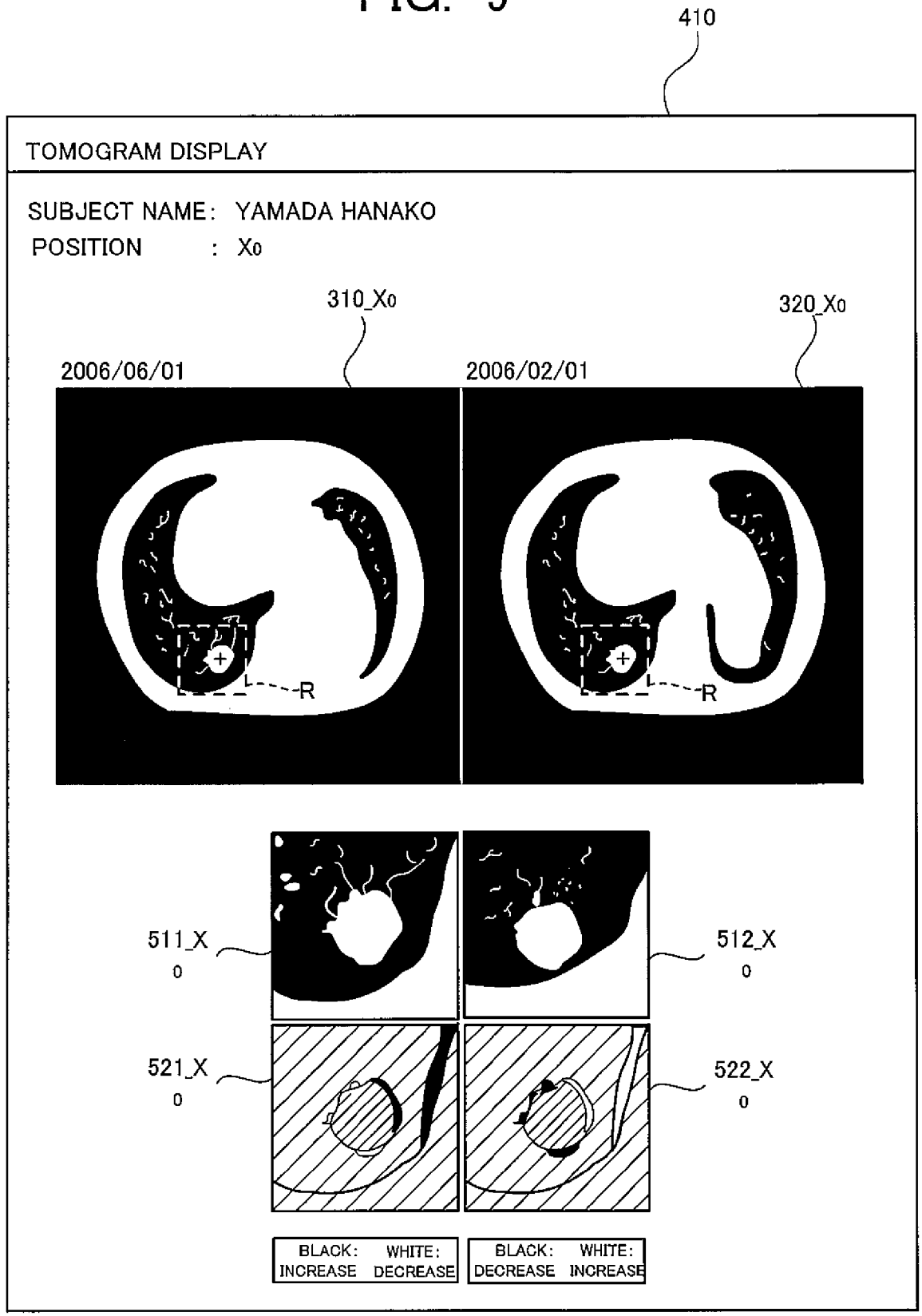
FIG. 9 illustrates an example of a tomogram display screen on which clipped images, a difference image and an inverse image are displayed.

FIG. 9 illustrates one example of the tomogram display screen 410 on which clipped images, a difference image and an inverse image are displayed.

On the tomogram display screen 410 depicted in FIG. 9, the tomograms 310_X0, 320_X0 at the same slicing position X0 are displayed, and further, clipped images 511_X0 and 512_X0 formed by cutting out the respective region-of-interest R from the tomograms 310_X0 and 320_X0, a difference image 521_X0 obtained between the clipped images 511_X0 and 512_X0, and an inverse image 522_X0 formed by inverting the concentration of the difference image 521_X0 are displayed arranged side-by-side. With the side-by-side display of the clipped images 511_X0 and 512_X0, it is possible to roughly recognize variations of the lesion easily. In the difference image 521_X0, an area where the lesion is increased is shown in black, whereas an area where the lesion is decreased is shown in white. And contrary to the difference image 521_X0, in the reverse image 522_X0, an area where the lesion is decreased is shown in black, whereas an area where the lesion is increased is shown in white. For people, black areas in images are easier to be recognized than white areas, and with the display of both the difference image 521_X0 and the reverse image 522_X0, the increase and decrease of the lesion can be easily confirmed. In this example, by checking the area shown in black in the difference image 521_X0, the increase and decrease of the lesion can be easily confirmed and also by checking the area shown in black in the reverse image 522_X0, the degree of reduction in the lesion can be easily confirmed.

By clicking the right button of the mouse 34, a gradation curve that represents gradation of the difference image 521_X0 and the inverse image 522_X0 is displayed. When the user corrects the gradation curve with the use of the mouse 34, the corrected gradation curve is transmitted from the gradation adjusting section 280 to the image displaying section 270 in FIG. 4 (step S5 in FIG. 5:Yes). The gradation adjusting section 280 corresponds to one example of the gradation adjusting section of the present invention.

The image displaying section 270 corrects the gradation of the difference image 521_X0 and the inverse image 522_X0 according to the gradation curve transmitted from the gradation adjusting section 280, and redisplays the corrected difference image 521_X0 and inverse image 522_X0 on the tomogram display screen 410 (step S6 in FIG. 5).

FIG. 10 illustrates how gradation is adjusted in a difference image.

As depicted in FIG. 10A, in the difference image 521_X0 before the adjustment of gradation, the difference between the clipped images 511_X0 and 512_X0 is close to "0", and since the concentration between the area shown in gray where variation of the lesion is little and the area shown in black where the lesion is increased is close, the difference between them is hard to be recognized in appearance. Adjusting the gradation curve to reduce the concentration of the gray area enables easier recognition of the black area as depicted in FIG. 10B and reliable detection of the increase in the lesion.

In a state shown in FIG. 9, if the user turns the wheel of the mouse 34, a switching of slicing position is instructed to the position-displacement correcting section 240 from the slicing position switching section 260 depicted in FIG. 4 (step S7 in FIG. 5: Yes).

The position-displacement correcting section 240 creates clipped images for a set of tomograms 310_Xm and 320_Xm at a slicing position Xm that is spaced apart in the direction of wheel rotation for a distance proportional to a rotating amount of the wheel from the slicing position X0 for the set of tomograms 310_X0 and 320_X0 that are currently displayed, and corrects position-displacement between the clipped images (step S3 in FIG. 5). The two clipped images of which position-displacement has been corrected are transmitted to the difference image creating section 250 and the image displaying section 270. At the difference image creating section 250, a difference image and an inverse image are created by using the two clipped images, and at the image displaying section 270, the clipped images, the difference image, and the inverse image are displayed on the tomogram display screen 410 (step S4 in FIG. 5).

Figure 11:
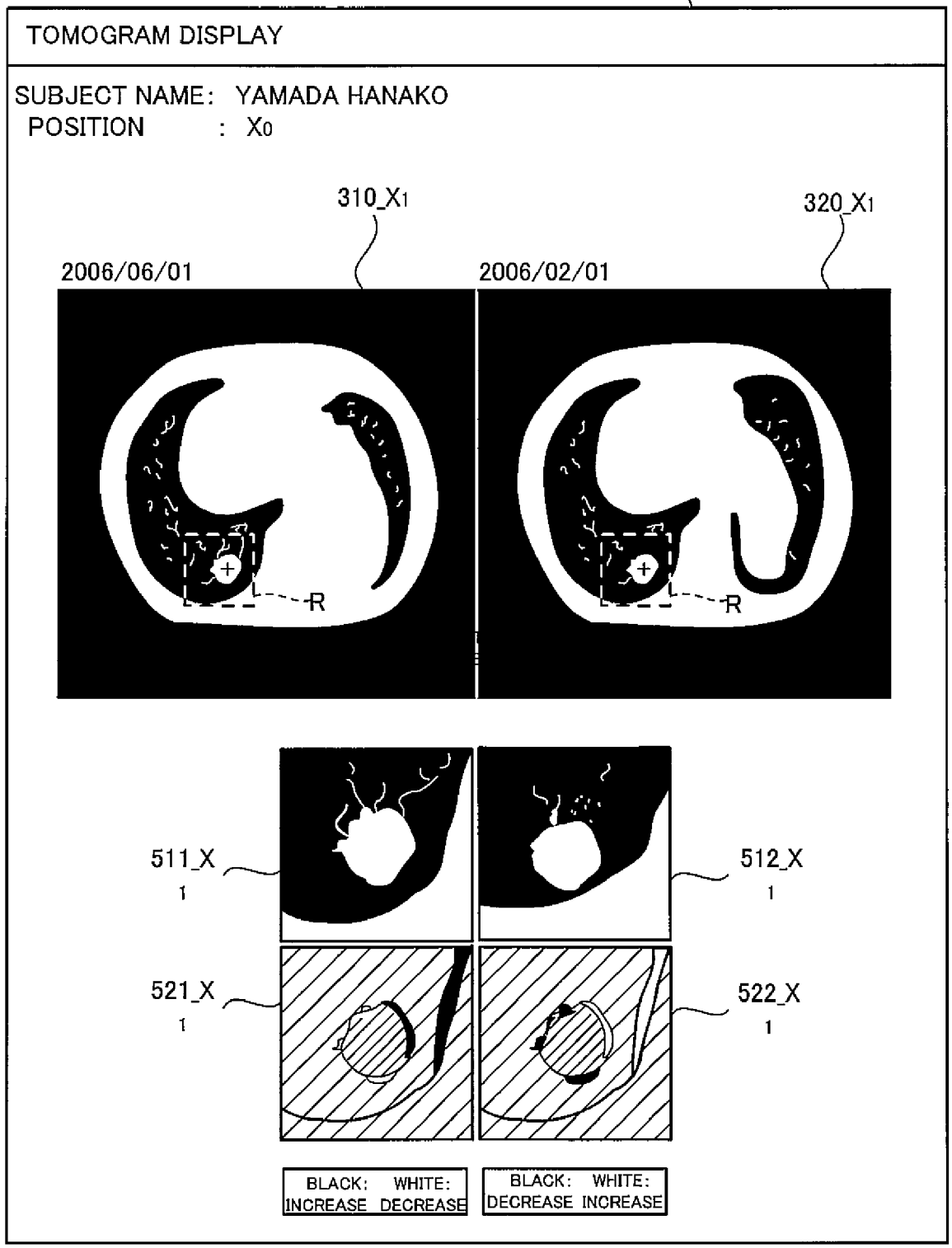
FIG. 11 illustrates an example of a tomogram display screen on which clipped images, a difference image and an inverse image at the slicing position X1 are displayed.

FIG. 11 illustrates an example of the tomogram display screen 410 on which clipped images, a difference image, and an inverse image at the slicing position X1 are displayed.

In this example, the wheel of the mouse 34 is rotated so as to advance the slicing position by one in step S7 in FIG. 5. FIG. 11 displays tomograms 310_X1 and 320_X1 at the slicing position X1 that is one position ahead of the slicing position X0 depicted in FIG. 9, clipped images 511_X1 and 512_X1 that are clippings of the regions-of-interest R on the tomograms 310_X1 and 320_X1, a difference image 521_X1 between the clipped images 511_X1 and 512_X1, and an inverse image 522_X1 of the difference image 521_X1. In this way, displaying by switching slicing positions by a user's instruction enables the user to recognize a lesion at various slicing positions and to grasp the shape and size of the lesion in three dimensions.

As described above, the medical image display unit 200 of the present embodiment enables the user to reliably recognize variations of a lesion or the like shown in respective medical images.

Now that the explanation of the first embodiment of the present invention is finished, an explanation will be given about a second embodiment of the present invention. Since the second embodiment differs from the first embodiment only in its displaying method of clipped images, same marks are used for the same elements and only different points will be explained.

In the medical image display device of the present embodiment, in the image displaying section 270 depicted in FIG. 4, the position for displaying clipped images created by the position-displacement correcting section 240 and the position for displaying a difference image and an inverse image created by the difference image creating section 250 are different from those of the first embodiment.

FIG. 12 illustrates an example of a tomogram display screen 410' on which clipped images, a difference image, and an inverse image are displayed.

On the tomogram display screen 410 of the first embodiment, as depicted in FIG. 9, the clipped images 511_X1 and 512_X1, the difference image 521_X1, and the inverse image 522_X1 are displayed so as not to overlap with the tomograms 310_X0 and 320_X0. However, as depicted in FIG. 12, on the tomogram display screen 410' of the present embodiment, a clipped image 512_X0 that is a clipping of the region-of-interest R from the other tomogram 320_X0 is displayed next to the region-of-interest R in the tomogram 310_X0 as well as the tomograms 310_X0 and 320_X0. In this way, by displaying the region-of-interest R in one tomogram and a clipped image cut out from the other tomogram arranged side by side in the one tomogram, it is possible to compare the regions-of-interest R in the two tomograms while confirming the position of the regions-of-interest R on the tomogram.

In the above, description is made about the example of displaying a difference image between two medical images; however, the image displaying section according to the present invention may display multiple difference images representing a difference among at least three medical images.

Further, in the above, description is made about the example of manually specifying on a medical image a region-of-interest the user suspects as a lesion; however, the region-of-interest setting section according to the present invention may search in medical images a region having an image pattern similar to a sample image through image processing and set the searched region as a region-of-interest.

Moreover, in the above, description is made about the example of creating a difference image by subtracting an image from another image, and conversely, creating an inverse image by subtracting the image of the subtracting side from the image of the subtracted side. However, the difference image creating section may create a difference image representing a difference between images and then create an inverse image by inverting the concentration of the difference image.

Additionally, in the above, description is made about the example of applying the image display device of the present invention to a diagnosis device; however, the image display device of the present invention may be applied to a management server or the like.

What is claimed is:

1. An image display device comprising:
   a region-of-interest setting section that sets two regions-of-interest respectively for two medical images representing a photographed subject;
   a difference image creating section that creates a difference image representing a difference between two image portions of the two regions-of-interest set by the region-of-interest setting section; and
   an image displaying section that retrieves one image portion of the two image portions from one medical image of the two medical images which includes the one image portion, and that displays on a same display screen the difference image as well as the two medical images arranged side by side with the difference image, while displaying the retrieved one image portion in such a manner that the retrieved one image portion overlaps with the other medical image of the two medical images which includes the other image portion of the two image portions and does not include the retrieved one image portion, the retrieved one image portion overlapping with the other medical image at a position next to the other image portion on the other medical image.

2. The image display device according to claim 1, wherein the region-of-interest setting section sets a region in response to an operation as the region-of-interest for a part of the two medical images, and for the rest of medical images except the part of the medical images, detects a region corresponding to the region in response to the operation to set as the region-of-interest.

3. The image display device according to claim 1, further comprising a position-displacement correcting section that corrects position-displacement of an image between the regions set by the region-of-interest setting section, and wherein the difference image creating section creates the difference image with the use of the image of which position-displacement has been corrected by the position-displacement correcting section.

4. The image display device according to claim 1, wherein the difference image creating section creates the difference image and an inverse image of which concentration is inverted from the difference image, and
the image displaying section displays the difference image and the inverse image arranged side by side.

5. The image display device according to claim 1, wherein the two medical images are photographed at different times for an identical subject.

6. The image display device according to claim 1, wherein the respective medical images correspond to a tomogram constituting a tomogram group when the subject is sliced at a plurality of slicing positions along a predetermined direction;
   the two medical images correspond to a set of tomograms having a common slicing position, which forms a different tomogram group;
   the region-of-interest setting section sets the region-of-interest for a tomogram in a set of the sets obtained at the plurality of slicing positions, and sets as the region-of-interest, for tomograms in another sets, a region corresponding to the region that has been set; and
   the image displaying section temporarily displays for a set, images of the regions-of-interest in tomograms of the set and a difference image between the images arranged side by side, and further, in response to a change operation, displays images of the regions-of-interest in tomograms of another sets as well as a difference image between the images arranged side-by-side.

7. The image display device according to claim 1, further comprising a gradation adjusting section that adjusts in response to an operation, gradation of a difference image displayed on the image displaying section.

* * * * *